United States Patent [19]

Seino et al.

[11] Patent Number: 4,614,718

[45] Date of Patent: Sep. 30, 1986

[54] SYNTHESIS OF SUGAR OR SUGAR-ALCOHOL FATTY ACID ESTERS

[75] Inventors: Hajime Seino, Tokyo; Tsuyoshi Uchibori, Yokohama; Sachiko Inamasu, Tokyo; Toshiyuki Nishitani, Ohmihachiman, all of Japan

[73] Assignee: Dai-Ichio Kogyo Seiyaku Co., Ltd., Kyoto, Japan

[21] Appl. No.: 640,892

[22] Filed: Aug. 14, 1984

[30] Foreign Application Priority Data

Aug. 23, 1983 [JP] Japan .................................. 58-154277
Apr. 25, 1984 [JP] Japan .................................. 59-84777

[51] Int. Cl.⁴ .......................... C12P 19/00; C12P 7/62; C12R 1/01; C12R 1/72; C12R 1/785
[52] U.S. Cl. .................................... 435/72; 435/135; 435/822; 435/921; 435/931
[58] Field of Search ............................ 435/72, 74, 135

[56] References Cited

U.S. PATENT DOCUMENTS 3,909,356 9/1975 Suzuki et al. .......................... 435/72
4,451,565 5/1984 Gatfield et al. .................. 435/135 X

OTHER PUBLICATIONS

Okamura et al, Biochimica et Biophysica Acta, vol. 575, pp. 156–165 (1979).
Seino et al, Journal American Oil Chemists Society, vol. 61 (11) 1761–1765 (1984).

*Primary Examiner*—Lionel M. Shapiro
*Attorney, Agent, or Firm*—Millen & White

[57] ABSTRACT

Sugar or sugar-alcohol fatty acid esters such as sucrose fatty acid esters are synthesized by incubating an aqueous mixture of a sugar or sugar-alcohol, a fatty acid and a catalytically active amount of a lipolytic enzyme, and recovering the resulting ester from the mixture.

11 Claims, No Drawings

SYNTHESIS OF SUGAR OR SUGAR-ALCOHOL FATTY ACID ESTERS

BACKGROUND OF THE INVENTION

Sugar or sugar-alcohol fatty acid esters such as sucrose fatty acid esters find uses in food industry as a nonionic surfactant. These esters have been conventionally synthesized by the transesterification of lower alkyl esters of fatty acids with sugars or sugar alcohols.

Several methods are known to produce sugar esters in a industrial scale. In a process generally known as the "solvent process", the fatty acid ester is reacted with sugar in a solvent such as dimethylformamide or dimethylsulfoxide in the presence of a basic transesterification catalyst. Another process known as the "microemulsion process" comprises the steps of dispersing the fatty acid ester in a solution of sugar in a solvent such as propylene glycol or water with the aid of an emulsifier such as soap and then removing the solvent before the transesterification takes place. A further process known as the "direct process" comprises reacting the fatty acid ester, the sugar and the basic transesterification catalyst in a molten mixture.

These known methods commonly require a high reaction temperature and thus the resulting products tend to color or darken with caramelized sugar. When dimethylformamide or dimethylsulfoxide is used, it makes the product unacceptable as a food additive.

It is a principal object of the present invention to provide a novel method for synthesizing sugar or sugar-alcohol esters of higher fatty acids which obviates the above-described disadvantages.

Other objects and advantages will become apparent as the description proceeds.

SUMMARY OF THE INVENTION

In accordance with the present invention, sugar or sugar-alcohol esters of higher fatty acids may be synthesized by incubating an aqueous mixture of a higher fatty acid, a sugar or sugar-alcohol and a catalytically active amount of a lipolytic enzyme at a temperature from about 20° C. to about 60° C. for a sufficient period of time to reach an equilibrium, and then recovering the resulting sugar or sugar-alcohol esters of the fatty acid from the mixture.

Thus the present invention enables the synthesis the sugar or sugar alcohol esters to be carried out in an aqueous medium at a temperature substancially lower than the caramerizing temperature of sugar or sugar alcohols.

DETAILED DESCRIPTION OF THE INVENTION

Examples of sugars which may be employed in the present invention include monosaccharides such as glucose, fructose, ribose, arabinose, mannose, xylose and galactose; disaccharides such as sucrose, maltose, cellobiose, lactose and treharose; trisaccharides such as maltotriose, raffinose, cellotriose and manninotriose; tetrasaccharides such as cellotetrose and stachyose; and polysaccharides such as dextrin, cyclodextrin, dextran, mannan, fructan, galactan, xylan, araban, cellulose and cellulose derivatives e.g. CMC, hydroxypropyl cellulose and methyl cellulose.

Examples of sugar-alcohols which may be used in the present invention include sorbitol, sorbitan, mannitol, xylitol, arabitol and dulcitol.

Examples of higher fatty acids include $C_8$–$C_{22}$ saturated fatty acid such as capric, lauric, myristic, palmitic and stearic acids; and $C_8$–$C_{22}$ unsaturated fatty acids such as oleic, linoleic and linolenic acids. Mixtures of fatty acids derived from naturally occurring oil and fats may also be used.

As is well-known, lipolytic enzymes may be derived from animal or microbial sources in the form of a complex with other hydrolytic enzymes and most of commercially available preparations thereof normally exhibit such other enzymatic activities in addition to the lipolytic activity. For example, pancreatin from pig pancreas contains amylolytic and proteolytic activities other than the lipolytic activity. Any commercial lipase preparation containing predominantly lipase activity may conveniently be used in the present invention although its more isolated or purified forms may also be used.

Various microbial lipase preparations are also commercially available and examples thereof include those obtained from genus Aspergillus, Pseudomonas, Enterobacterium, Chromobacterium, Geotrichum, Penicillium, Mucor, Candida, Rhizopus and the like.

The esterification reaction may be carried out by adding the substrates and the enzyme to a buffer and incubating the mixture. Preferable pH ranges may vary with the optimal pH range of particular enzyme preparations and are generally between 4 and 9, preferably between 5 and 8. Phosphate buffers having these pH ranges are preferable.

The molar ratio of sugar or sugar-alcohol to the higher fatty acid may vary from 1:1 to 1:6. The total substrate and enzyme concentrations in the buffer may range from 1 to 30% (wt./vol.). Since higher fatty acids are not soluble in the buffer, they are added to the buffer as finely divided particles or by emulsifying the fatty acid in the buffer using an emulsifier which does not depress the enzymatic activity such as soaps. The incubation temperature may range between about 20° C. and about 60° C., preferably between about 30° C. and about 50° C.

The amount of the lipolytic enzyme relative to that of the substrates is not critical and thus may vary over a wide range depending upon the nature and potencies of particular enzyme preparations. Generally 10 to 200% by weight relative to the sugar or sugar-alcohol may be employed. The upper limit is a matter of economy. Since the esterification reaction involved is reversible, the reaction eventually reaches an equilibrium. The incubation is terminated when this point is reached, and the desired ester may be recovered and purified in a manner known per se.

It is contemplated that the principle of the present invention may be realized by the use of immobilized enzyme preparations such as those immobilized into microcapsules or matrices, or covalently bonded to a suitable water-insoluble carrier. In this case, the purification of the resulting sugar or sugar-alcohol esters may be greatly simplified. Also, the reaction may be carried out in a continuous mode by passing the substrate solution through a reactor containing the immobilized enzyme. The immobilized enzyme may be used repeatedly.

It will be appreciated from the foregoing description that the present invention has several important advantages over the known purely chemical transesterification methods. It avoids the use of relatively high reaction temperatures to obtain colorless products. The use of aqueous reaction media renders the products safer and more acceptable for use as a food additive. The use of free fatty acid eliminates the need for preparing the starting lower alkyl esters and also for removal of harmful by-products such as methanol during the transesterification reaction.

The following examples will further illustrate the present invention.

EXAMPLE 1

To 1000 ml of a phosphate buffer having a pH of 5.4 were added 2.0 g of a commercial lipase preparation (a microbial lipase originating from Candida cylindracea sold under the name of LIPASE MY by Meito Sangyo K.K., Nagoya, Japan), 3.4 g of sucrose and 11.3 g of oleic acid. The mixture was incubated at 40° C. with stirring for 72 hours.

The mixture was then lyophilized and the resulting solid was extracted with chloroform. The chloroform extract was concentrated in vacuo. The concentrate was added to an amount of tetrahydrofuran and insoluble matters were separated by centrifuging the mixture at 3000 rpm. The tetrahydrofuran solution was fractionated by means of gel permeation chromatography and fractions containing a first peak were collected. After evaporating the solvent, 7.69 g of sucrose oleate was obtained.

EXAMPLE 2

The procedure of Example 1 was repeated except that 11.6 g of stearic acid was substituted for 11.3 g of oleic acid. 6.23 g of sucrose stearate was obtained.

EXAMPLE 3

To 1000 ml of a phosphate buffer having a pH 7.3 were added 3.6 g of glucose, 22.0 g of oleic acid and 4.0 g of LIPASE MY. The mixture was incubated at 40° C. with stirring for 72 hours. The reaction mixture was processed as in Example 1 and 10.67 g of glucose oleate was obtained.

EXAMPLE 4

The procedure of Example 3 was repeated except that 3.6 g of fructose was substituted for 3.6 g of glucose. 12.17 g of fructose oleate was obtained.

EXAMPLE 5

To 1000 ml of a phosphate buffer having pH of 5.4 were added 2.0 g of LIPASE MY, 22.56 g of oleic acid 3.64 g of sorbitol. The mixture was incubated at 40° C. with stirring for 72 hours. The reaction mixture was processed as in Example 1 and 7.49 g of sorbitol oleate was obtained.

EXAMPLE 6

The procedure of Example 5 was repeated except that 22.8 g of stearic acid was substituted for 22.56 g of oleic acid. 6.27 g of sorbitol stearate was obtained.

EXAMPLE 7

To 1000 ml of a phosphate buffer having a pH of 7.3 were added 5.46 g of sorbitol, 22.56 g of oleic acid and 4.0 g of LIPASE MY. The mixture was incubated and processed as in Example 1. 16.92 g of sorbitol oleate was obtained.

EXAMPLE 8

The procedure of Example 7 was repeated except that 3.28 g of sorbitan was substituted for 5.46 g of sorbitol and the enzyme preparation was descreased to 2.0 g. 8.65 g of sorbitan oleate was obtained.

EXAMPLE 9

To 1000 ml of a phosphate buffer having a pH of 7.3 were added 4.93 g of sorbitan, 22.60 g of oleic acid and 4.0 g of LIPASE MY. The mixture was incubated and processed as in Example 1 to give 18.34 g of sorbitan oleate.

EXAMPLE 10

The procedure of Example 1 was repeated except that 3.64 g of mannitol and 2.0 g of a commercial lipase preparation derived from Rhizopus delemar (TALIPASE sold by Tanabe Seiyaku Co., Ltd., Osaka, Japan) were used. 6.60 g of mannitol oleate was obtained.

EXAMPLE 11

The procedure of Example 1 was repeated except that 3.00 g of xylose was replaced for 3.4 g of sucrose. 5.81 g of xylose oleate was obtained.

EXAMPLE 12

The procedure of Example 1 was repeated except that 6.84 g of treharose was substituted for 3.4 g of sucrose. 5.49 g of treharose oleate was obtained.

EXAMPLE 13

The procedure of Example 1 was repeated except that 10.08 g of raffinose was substituted for 3.4 g of sucrose. 6.65 g of raffinose oleate was obtained.

EXAMPLE 14

The procedure of Example 1 was repeated except that 13.34 g of cellotetrose was replaced for 3.4 g of sucrose. 7.53 g of cellotetrose oleate was obtained.

EXAMPLE 15

The procedure of Example 3 was repeated except that 10 g of carboxymethyl cellulose (D.S.=0.6) was substituted for 3.6 g of glucose. 4.62 g of CMC oleate was obtained.

We claim:

1. A method for producing a sugar or sugar alcohol ester of a higher fatty acid which comprises the steps of incubating an aqueous mixture of a $C_8$–$C_{22}$ fatty acid, a sugar or sugar alcohol and a catalytically active amount of a lipolytic enyme derived from the genus Pseudomonus, Enterobacterium, Chromobacterium, Mucor or Candida at a temperature from about 20° C. to about 60° C. for a sufficient time to reach an equilibrium to produce said ester, and recovering said ester from the mixture.

2. The method according to claim 1, wherein said fatty acid is capric, lauric, myristic, palmitic, stearic, oleic linoleic, linolenic acid or a mixture of these acids.

3. The method according to claim 1, wherein said sugar is a mono-, di-, tri-, tetra- or polysaccharide.

4. The method according to claim 3, wherein said sugar is glucose, fructose or sucrose.

5. The method according to claim 3, wherein said sugar alcohol is sorbitol, sorbitan, mannitol, xylitol, arabitol or dulcitol.

6. The method according to claim 1, wherein said incubation is carried out in a buffer having a pH from 4 to 9.

7. The method according to claim 6, wherein the molar ratio of said fatty acid to said sugar or sugar alcohol is from 1:1 to 1:6.

8. The method of claim 7, wherein the amount of said enzyme is from 10% to 200% by weight relative to said sugar or sugar alcohol.

9. The method of claim 8, wherein said fatty acid, said sugar or sugar alcohol and said enzyme are present in total at a concentration from 1 to 30 wt./vol. % in said aqueous mixture.

10. The method of claim 9, wherein said pH is from 5 to 8, and said temperature is from about 30° C. to about 50° C.

11. The method of claim 1, wherein said enzyme is immobolized.

* * * * *